United States Patent
Thomas et al.

(10) Patent No.: US 7,869,051 B2
(45) Date of Patent: Jan. 11, 2011

(54) SYSTEM AND METHOD FOR RATIOMETRIC NON-LINEAR COHERENT IMAGING

(75) Inventors: James L. Thomas, Cedar Crest, NM (US); Wolfgang G. Ruldolph, Albuquerque, NM (US); Xuejun Liu, Albuquerque, NM (US)

(73) Assignee: STC. UNM, Albuquerque, NM (US)

( * ) Notice: Subject to any disclaimer, the term of this patent is extended or adjusted under 35 U.S.C. 154(b) by 442 days.

(21) Appl. No.: 12/016,711

(22) Filed: Jan. 18, 2008

(65) Prior Publication Data

US 2008/0225269 A1 Sep. 18, 2008

Related U.S. Application Data

(60) Provisional application No. 60/881,289, filed on Jan. 19, 2007.

(51) Int. Cl.
*G01B 9/02* (2006.01)
*G01J 3/45* (2006.01)
*G01J 3/44* (2006.01)

(52) U.S. Cl. ...................... 356/456; 356/301

(58) Field of Classification Search .............. 356/301, 356/451, 456, 484
See application file for complete search history.

(56) References Cited

U.S. PATENT DOCUMENTS

| | | | | |
|---|---|---|---|---|
| 4,405,237 A | * | 9/1983 | Manuccia et al. | 356/301 |
| 6,108,081 A | * | 8/2000 | Holtom et al. | 356/301 |
| 6,798,507 B2 | * | 9/2004 | Xie et al. | 356/301 |
| 6,809,814 B2 | * | 10/2004 | Xie et al. | 356/301 |
| 7,573,577 B2 | * | 8/2009 | Martinez | 356/451 |

* cited by examiner

*Primary Examiner*—Michael A Lyons
(74) *Attorney, Agent, or Firm*—The Adams Kennedy Law Firm, LLC

(57) ABSTRACT

The present invention includes a system and method for coherent imaging. The system of the present invention includes a light source adapted to provide coherent light to illuminate a sample resulting in optically mixed coherent signals and a detector adapted to receive the optically mixed coherent signals and produce an output signal in response thereto. The optically mixed coherent signals will be a set of sum and difference frequency combinations of the frequencies in the coherent light. A processor is connected to the detector and adapted to ratio a selected two of the optically mixed coherent signals in response to the output signal received by the detector and to generate an image in response to the ratioed optically mixed coherent signals, which can be displayed for a user.

17 Claims, 6 Drawing Sheets

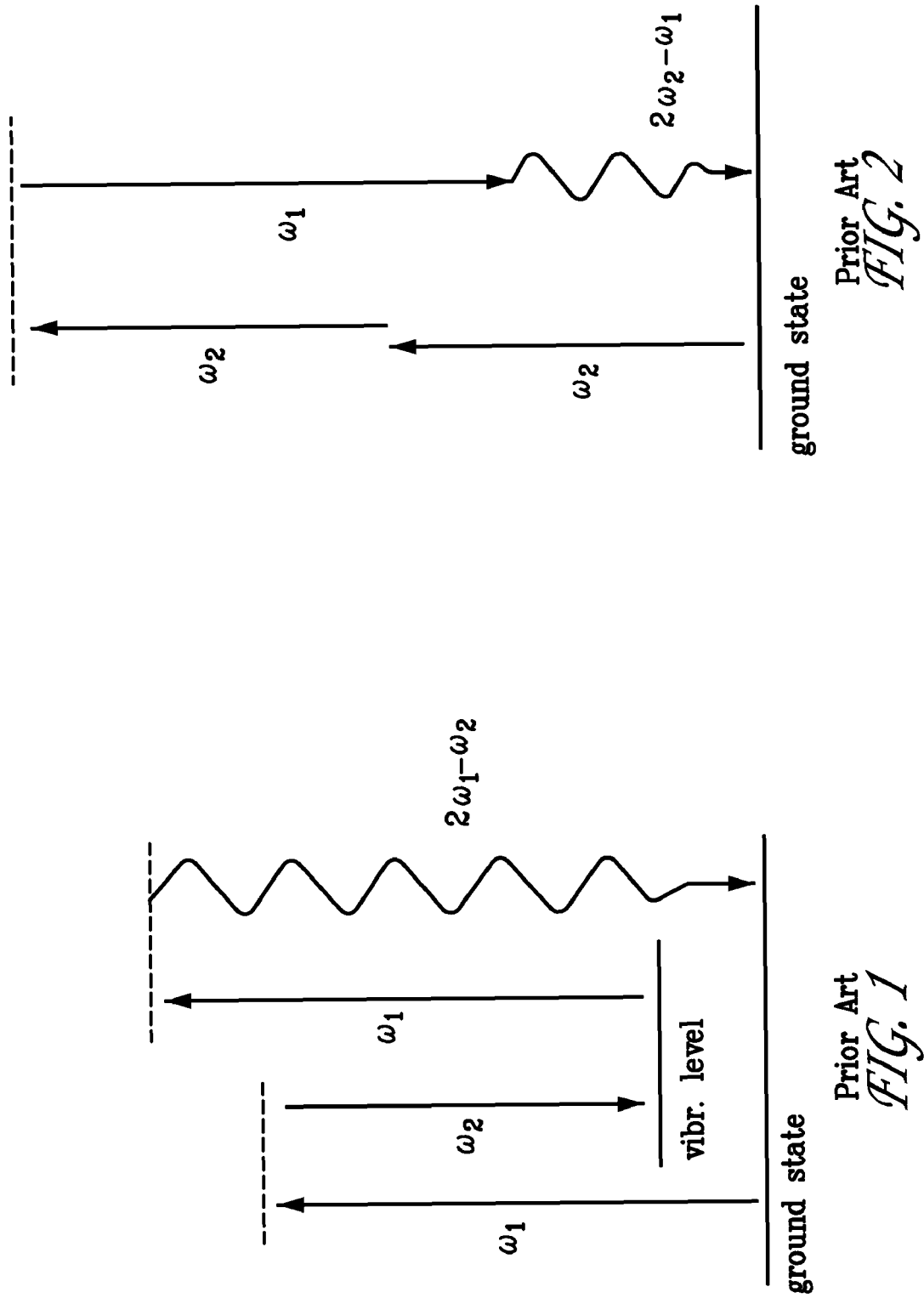

SYSTEM AND METHOD FOR RATIOMETRIC NON-LINEAR COHERENT IMAGING

CLAIM OF PRIORITY UNDER 35 U.S.C. §119

The present application for patent claims priority to Provisional Application No. 60/881,289 entitled "Ratiometric Method for Non-linear Coherent Imaging," filed Jan. 19, 2007, and assigned to the assignee hereof and hereby expressly incorporated by reference herein.

CONTRACTUAL ORIGIN OF THE INVENTION

This invention was made with government support under grant no. W911NF-05-1-0464 awarded by the Army Research Office. The government has certain rights in this invention.

BACKGROUND

1. Field of the Present Invention

The present invention relates generally to the field of imaging, and more particularly to the field of non-linear coherent imaging.

2. History of the Related Art

Non-linear coherent imaging refers to any imaging technique in which multiple input photons are coherently combined to produce each output photon. In general, in any optically non-linear medium, photons of all sum and difference frequencies will be produced. For example, FIG. 1 illustrates an energy level diagram for a process known as Coherent Anti-Stokes Raman Spectroscopy (CARS) in which a vibrational state of a target molecule results in the resonant enhancement of photon generation at a frequency $2\omega_1-\omega_2$. In general the strength of any signal produced at a given sum/difference frequency depends on whether molecular or atomic energy levels can give rise to resonant enhancement. The strengths of different sum/difference signals depend on the detailed vibrational and electronic energy levels of the molecule being probed. For example, a process called Stimulated Parametric Fluorescence shown in FIG. 2 will be stronger when the molecule or material has an energy level close to the top level shown therein. In such a case, the existence of a molecular excited state with energy near the top level in FIG. 2 will resonantly enhance an output a $2\omega_2-\omega_1$. FIGS. 3A and 3B illustrate second and third harmonic signals generated by a single input frequency, $\omega_1$.

In spite of the numerous enhancements in spectroscopy and microscopy in the recent past, the aforementioned processes lack in their ability to generate image contrast for a sample illuminated with coherent light. Given the inherent complexity in non-linear coherent imaging, it is desirable to provide image contrast in a manner that is both cost-effective and easily reproducible. As such, there is a need in the art for a coherent imaging system and/or method that is capable of generating image contrast in an efficient and effective manner.

SUMMARY OF THE PRESENT INVENTION

Accordingly, the present invention includes a system and method for coherent imaging that are adapted for generating image contrast. The system of the present invention includes a light source adapted to provide coherent light to illuminate a sample, resulting in optically mixed coherent signals and a detector adapted to receive the optically mixed coherent signals and produce an output signal in response thereto. As described more fully below, the output signal corresponds to any two frequencies of light in the optically mixed coherent signal. The system can also include a processor connected to the detector and adapted to ratio the optically mixed coherent signals in response to the output signal received by the detector and to generate an image in response to the ratioed optically mixed coherent signals. The system can further include a display connected to the processor and adapted to display the image generated by the processor. The system of the present invention can also function using a single input frequency of light, in which the light source is adapted to illuminate a sample with light resulting in optically mixed coherent output signals.

In another aspect, the present invention includes a method for coherent imaging including the steps of illuminating a sample with coherent light, thereby causing the sample to generate optically mixed coherent signals and receiving the optically mixed coherent signals from the illuminated sample. The method can also include the steps of ratioing the optically mixed coherent signals and generating an image in response to the ratioed optically mixed coherent signals.

Many other aspects, features and advantages of the present invention are described in detail below with reference to the following figures.

BRIEF DESCRIPTION OF THE FIGURES

FIG. 1 is an energy-level diagram illustrating an interaction between a first combination of coherent light and a sample.

FIG. 2 is an energy level diagram illustrating an interaction between a second combination of coherent light and a sample.

DETAILED DESCRIPTION OF THE PREFERRED EMBODIMENTS

The following description of the preferred embodiments is provided to enable any person skilled in the art to make or use the present invention. Various modifications to these embodiments will be readily apparent to those skilled in the art, and the generic principles defined herein may be applied to other embodiments without departing from the spirit or scope of the invention as set forth in the appended claims.

Figure 3B:
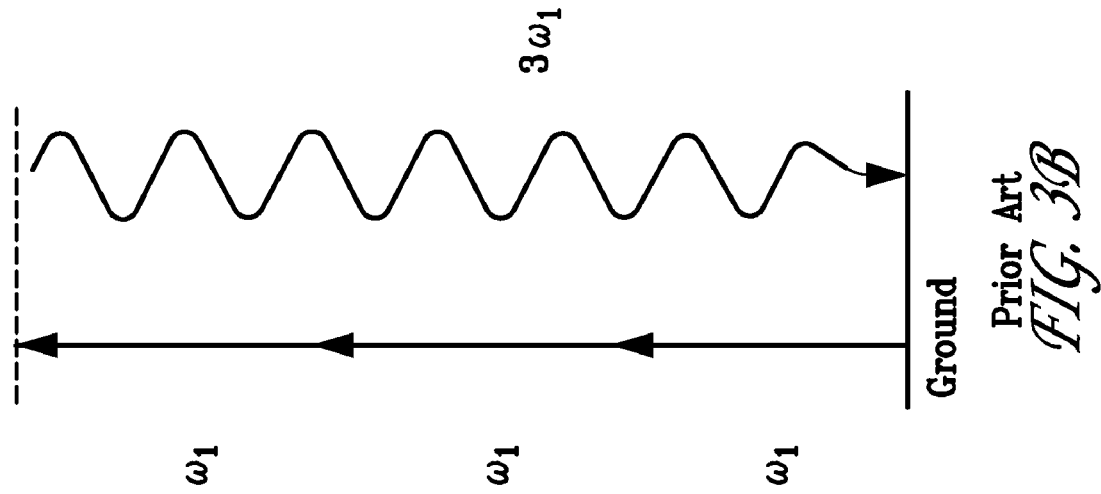
FIGS. 3A and 3B are energy level diagrams illustrating an interaction between a single frequency group of photons and a sample.
Figure 3A:
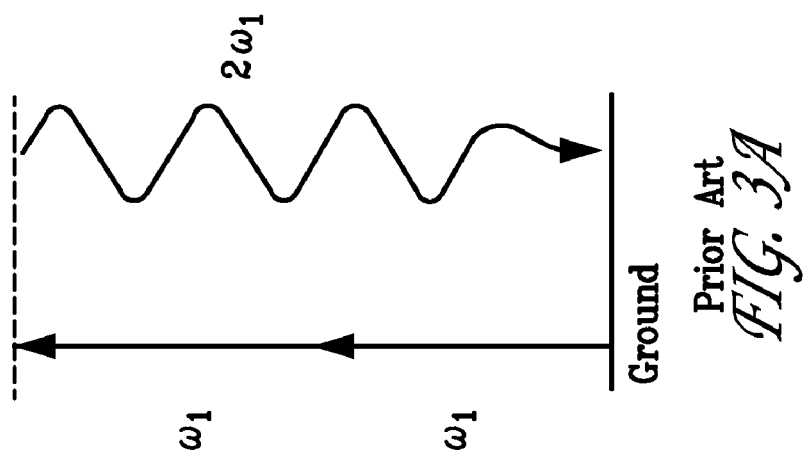
Figure 4:
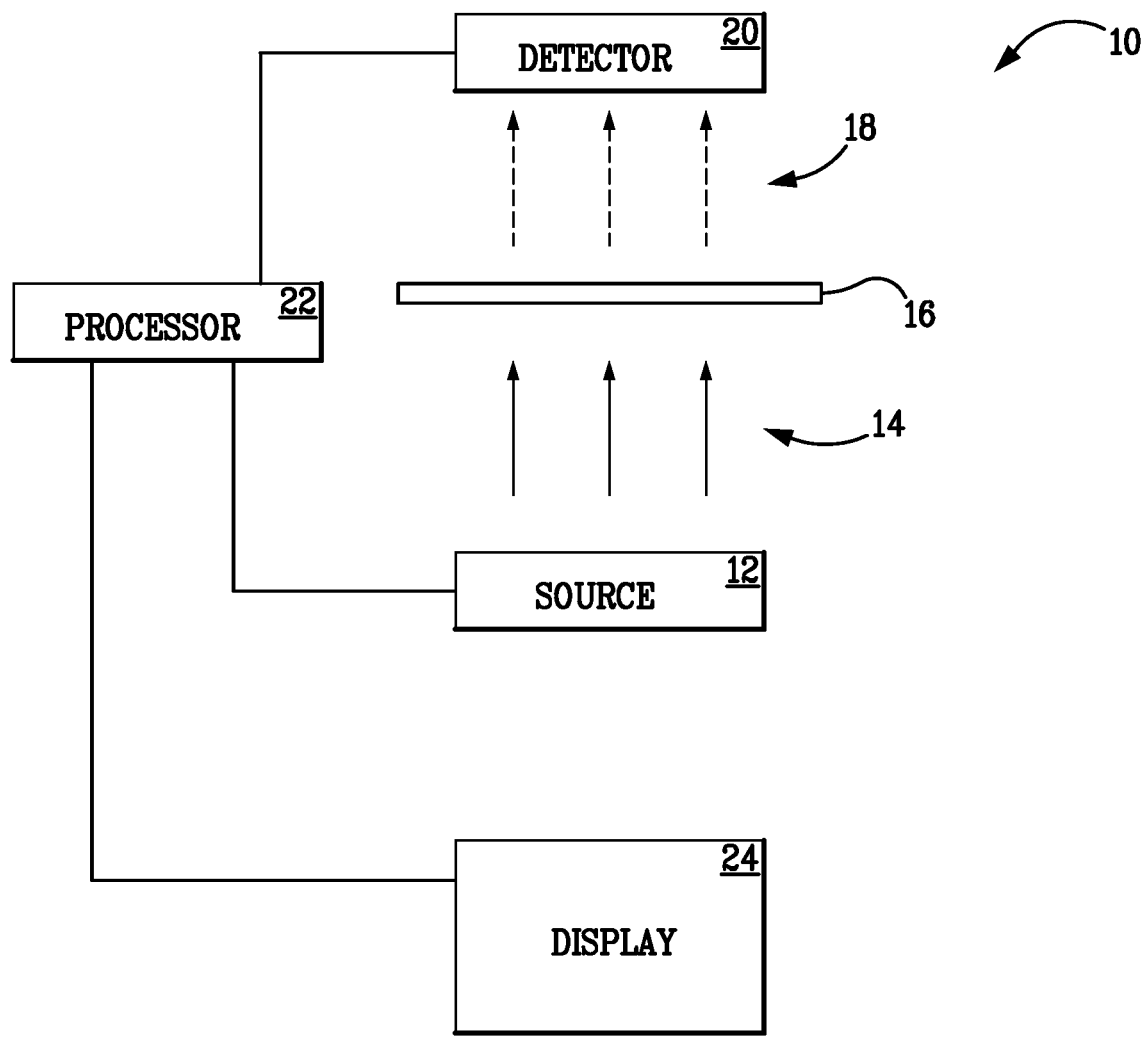
FIG. 4 is a schematic block diagram of a system for coherent imaging in accordance with a preferred embodiment of the present invention.

The present invention includes a system and method for coherent imaging. As shown in FIG. 4, a system 10 of the preferred embodiment includes a light source 12 adapted to provide coherent light 14. As used herein, the term coherent light denotes a combination of photons that can combine and interfere either constructively or destructively. The light source 12 can be a single frequency light source, a coherent light source of multiple frequencies, or a combination of single frequency light sources that constructively form a coherent beam of light. Suitable light sources 12 can include for example lasers, light emitting diodes or any other source for which the frequency or frequencies of light is known. The coherent light 14 emanated from the light source 12 can be directed such that it illuminates a sample 16 resulting in two or more optically mixed coherent signals 18, each of which is a sum/difference combination of the frequencies of light in the coherent light 14.

The system 10 can further include a detector 20 adapted to receive the optically mixed coherent signals 18 and produce an output signal in response thereto. The detector 20 functions to receive photonic inputs emanated from the illuminate sample 16 and produce an output signal that corresponds to two frequencies of light in the optically mixed coherent signals 18. The detector 20 can be any suitable type of detector for use in imaging, such as for example a photodetector, a photodiode, an avalanche photodiode, a photomultiplier tube, a charge-coupled device or any combination, arrangement or array of the foregoing. The detector 20 can include any suitable filters, whether optical or electronic, as well as any suitable circuitry for converting the photonic inputs into an output signal usable by the system 10.

The system 10 can also include a processor 22 connected to the detector 20. The processor 22 can be adapted to ratio the optically mixed coherent signals 18 received by the detector 20 and to generate an image in response to the ratioed optically mixed coherent signal. The processor 22 can include any general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination designed to perform the functions described in this document. The processor 22 functions to receive an output signal from the detector 20, wherein such output signal corresponds to two or more frequencies in the optically mixed coherent signals 18, and to ratio two frequencies of light within the optically mixed coherent signals 18. As used herein, the term ratio can include, for example, a mathematical operation in which a quantity of one frequency of photons is divisible by another quantity of another frequency of photons.

For example, the ratio can be a ratio of the quantity of photons in the optically mixed coherent signals 18 that are of the same frequency of those in the coherent light 14. That is, if the coherent light 14 is composed of photons of frequency A and photons of frequency B, then the optically mixed coherent signals 18 will be a set of sum/difference frequencies combinations, such as for example 2A–B, 3B–A, etc. Accordingly, the ratioing function will produce a ratio of the number of photons of one frequency combination to the number of photons of another frequency combination in the optically mixed coherent signals 18. The ratioing described herein can be indicative of the atomic energy levels, molecular energy levels and various vibrational states of the sample 16, and can be used to identify particular features or aspects of the sample 16 for use in increasing the image contrast in a coherent image. Moreover, as discussed further herein, different components, molecules or compounds within a sample might have differing ratios computed by the processor 22, which will aid in generating image contrast between two or more differing materials that might otherwise have optically similar characteristics.

Alternatively, the system can include a single frequency light source 12 which produces a single frequency of light as opposed to coherent light 14. In this alternative embodiment, the single frequency input light will still cause the sample 16 to produce two or more optically mixed coherent signals 18, each of which being a different sum/difference combination of the single frequency of light. In response thereto, the ratioing function will produce the ratio of any two sum/difference frequency combinations of the input frequency.

The processor 22 can be further connected to the light source 12 and adapted to control the coherent light 14 output of the light source 12. In one variation of the system 10 of the preferred embodiment, the processor 22 can be adapted to vary the coherent light 14 output of the light source 12 as a function of time, e.g. to vary the frequency combinations of the coherent light 14 output by controlling one or more discrete elements of the light source 12. For example, the light source 12 can include a visible light laser operable at 790 nanometers (nm) and an infrared laser operable at 1037 nm, the combined outputs of which result in the coherent light 14. The processor 22 can be adapted to control the characteristics of the coherent light 14 by varying the relative outputs of the two example lasers, which in turn can result in different resonant and imaging characteristics of the sample 16.

The system 10 of the preferred embodiment can also include a display 24 connected to the processor 22 and adapted to display the image generated by the processor 22. The display 24 can include any suitable means, apparatus or machine for receiving electrical data and presenting it in a visible and/or audible format such that a user of the system 10 of the preferred embodiment can receive desirable data concerning the sample 16.

In another variation of the system 10 of the preferred embodiment, the system 10 can include an optical element (not shown) or any combination of optical elements to focus the coherent light 14 onto the sample 16. Example optical elements include mirrors, lenses, slits, gratings, filters as well as any other individual optical component or combination thereof that is usable in the optical sciences for controlling a direction, beam width, intensity, frequency, or focal point of a beam of light, such as the coherent light 14.

In another preferred embodiment, the light source 12 of the system 10 can include a single frequency light source, such as a single frequency laser, light emitting diode or the like. A single frequency of light can generate coherent signals within a sample, the ratio of which can be determined by the processor 22 in order to generate image contrast in the resultant image. For example, a single frequency laser can generate second and third harmonic coherent signals in a sample, the ratio of which can be determined by the processor 22 in order to generate image contrast as noted above.

Figure 5:
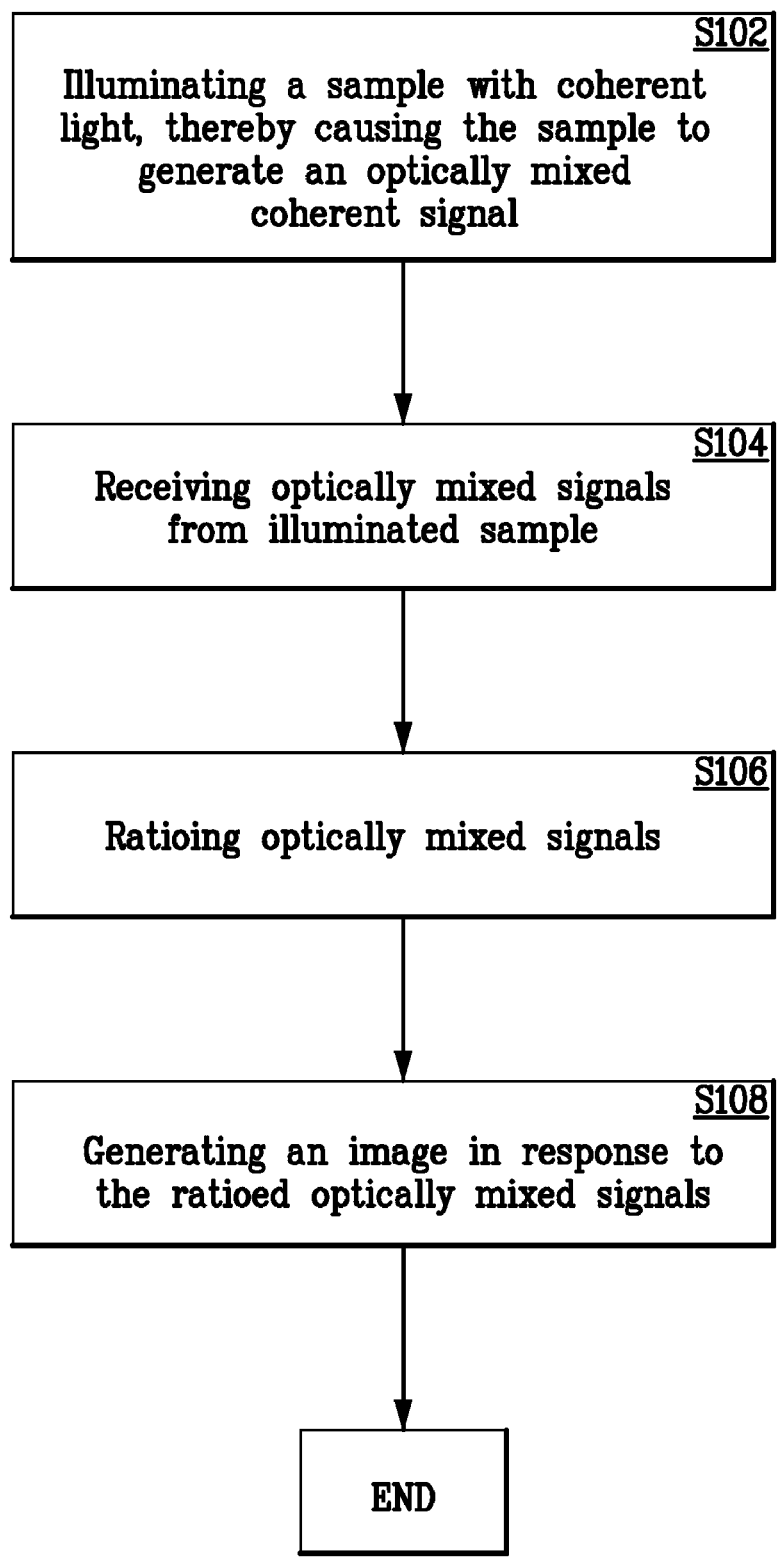
FIG. 5 is a flowchart depicting a method for coherent imaging in accordance with another preferred embodiment of the present invention.

FIG. 5 is a flowchart depicting a method of coherent imaging in accordance with a preferred embodiment of the present invention. The method recites in step S102 illuminating a sample with coherent light, such as for example using two or more lasers having predetermined and distinct frequencies. As noted above, when a sample is illuminated with coherent light, the sample can generate two or more optically mixed coherent signals that can be indicative of atomic energy levels, molecular energy levels and/or vibrational states of the sample. Step S104 of the method of the preferred embodiment recites receiving the two or more optically mixed coherent signals from the illuminated sample. Step S104 can be performed by a detector of the type described herein, including for example a photodetector, a photodiode, an avalanche photodiode, a photomultiplier tube, a charge-coupled device or any combination, arrangement or array of the foregoing.

Step S106 recites ratioing the optically mixed coherent signals, which can include performing a mathematical operation to determine a proportional relationship between two sum/difference frequencies of light that make up the optically mixed coherent signals. In step S108, the method of the preferred embodiment recites generating an image in response to the ratioed optically mixed coherent signals, wherein the image can be stored and/or displayed for the convenience of a user. As noted above, the ratioed optically mixed coherent signals can contain important information concerning the atomic energy levels, molecular energy levels and/or vibrational states of the sample. Moreover, the ratioed optically mixed coherent signals be further utilized to provide far greater image contrast in an image generated according to step S108, which will aid a user in discriminating between materials having otherwise optically similar properties.

In a first variation of the method of the preferred embodiment, the step of illuminating a sample with coherent light can include controlling at least two lasers at predetermined frequencies in order to generate the coherent light. A processor of the type described herein can be adapted to control the at least two lasers to vary the timing, ratio, intensity or other aspect of the at least two lasers that form the coherent light.

In a second variation of the method of the preferred embodiment, the method can include the step of focusing the coherent light onto the sample. The focusing step can be performed by any suitable optical element or any combination of optical elements to focus the coherent light onto the sample. Example optical elements noted above include mirrors, lenses, slits, gratings, filters as well as any other individual optical component or combination thereof that is usable in the optical sciences for controlling a direction, beam width, intensity, frequency, or focal point of a beam of light, such as the coherent light.

In a third variation of the method of the preferred embodiment, the method can include the step of varying a combination of the coherent light. The varying step can be performed by a processor of the type described herein that is adapted to control one or more sources of the coherent light and can thereby control a mixture of frequencies that compose the coherent light. For example, the processor can vary the input combinations of the coherent light such that the step of ratioing the optically mixed coherent signal is performed at least in part in response to the varying combinations of the coherent light. Alternatively, the varying step can include causing the processor to vary a pulse duration of at least two lasers operating at predetermined frequencies, such that the resultant coherent light is composed of different portions of the respective laser light.

Any machine-readable medium tangibly embodying instructions may be used in implementing the one or more steps in the methodologies described in this document. As a non-exclusive example, software codes may be stored in a memory or database or storage unit, and executed by the processor 22 described herein. Memory may be implemented within the processor 22 or external to the processor 22. As used in this document, the term "memory" refers to any type of long term, short term, volatile, nonvolatile, or other memory and is not to be limited to any particular type of memory or number of memories, or type of media upon which memory is stored.

Figure 6B:
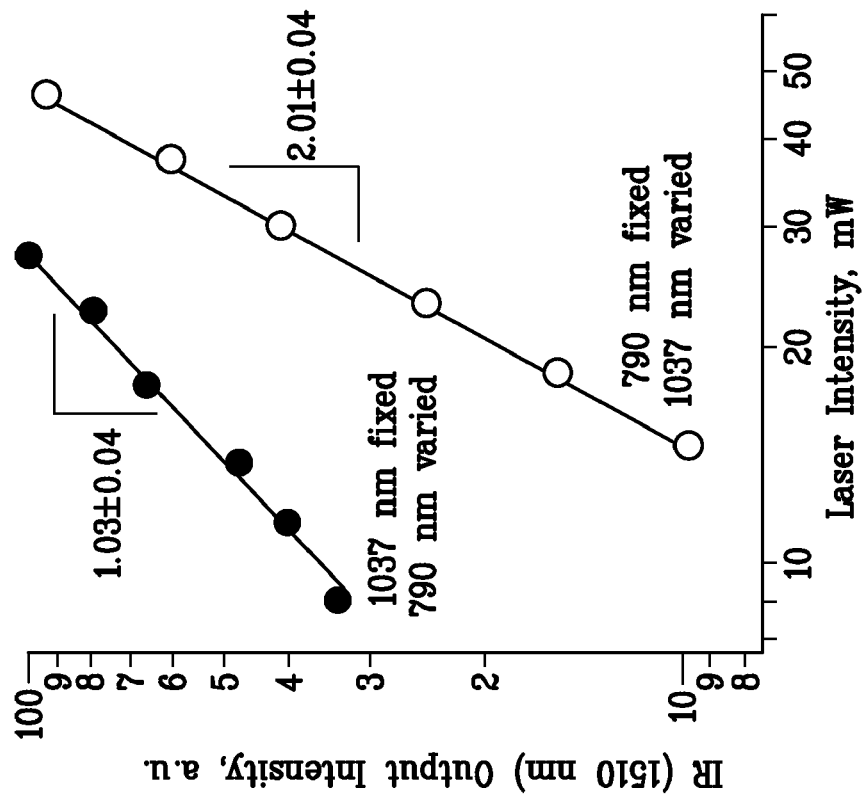
FIGS. 6A and 6B are logarithmic graphical representations of a coherent light output in response to a coherent light input.
Figure 6A:
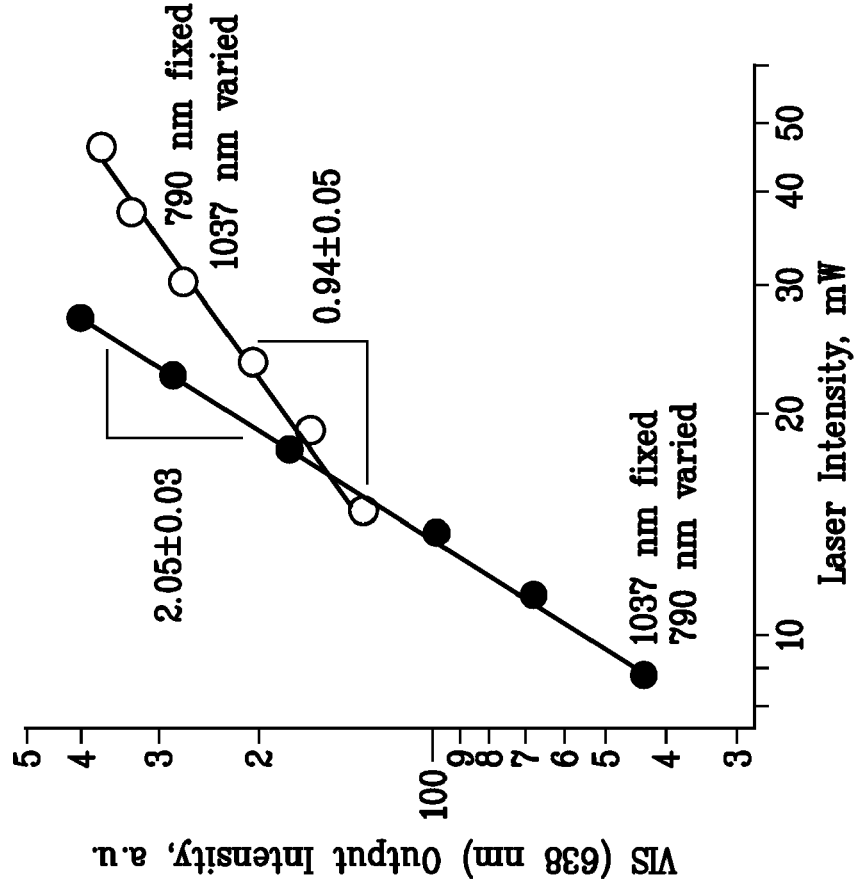

An example system and method was employed by the inventors in order to test the precision and advantages of the preferred embodiments described herein. FIGS. 6A and 6B are logarithmic graphical representations of an output intensity as a function of an input laser intensity. As shown in FIG. 6A, a 638 nm visible output intensity varies quadratically with an 790 nm input illumination and linearly with a 1037 nm input illumination, confirming that the underlying non-linear process requires two 790 nm photons for each 1037 nm photon. On the other hand, FIG. 6B shows that an infrared 1510 nm output intensity varies quadratically with a 1037 nm input illumination and linearly with a 790 nm input illumination, confirming that the underlying non-linear process requires two 1037 nm photons for each 790 nm photon.

Figure 7:
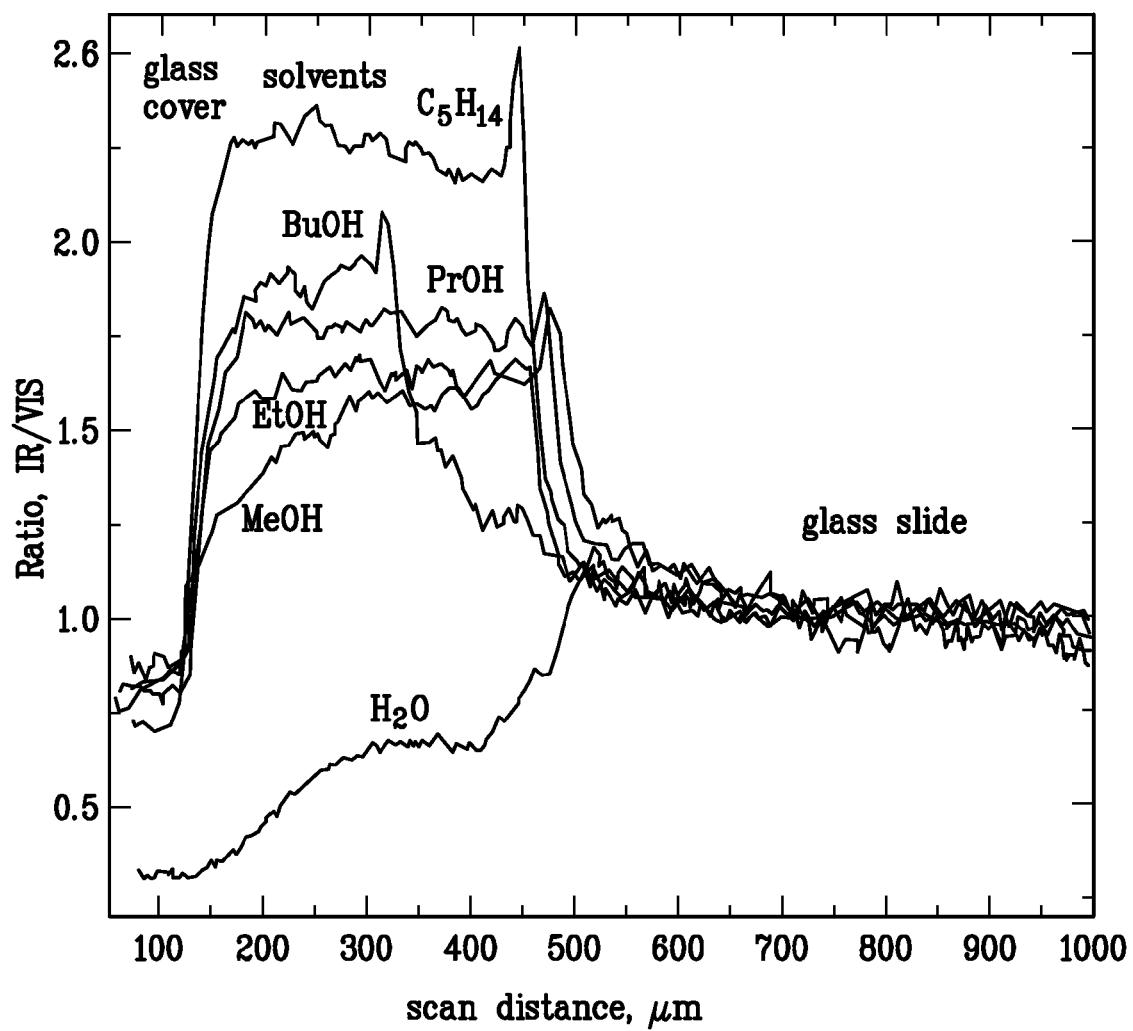
FIG. 7 is a graphical representation of data illustrating how a ratio of optically mixed coherent signals having infrared and visible frequency combinations depends on the specific material for a plurality of sample materials.

FIG. 7 is a graphical representation of the optically mixed coherent signal (infrared to visible) as a function of a scan distance or depth of laser focus in each sample. In the experiment represented in FIG. 7, significant multi-photon signals are generated only at the focus of the lasers, providing optical sectioning capability. As shown, each of the plurality of solvents generates different ratios of sum/difference output signals at each scan distance. As the proportionality between detector output and signal input (in photon count or energy) may vary between detectors, the glass slide is normalized to a ratio of approximately one for comparison among the plurality of differing materials. For example, at a scan distance of approximately 200 micrometers water generates an infrared to visible ratio of approximately 0.5, methyl alcohol (MeOH) generates an infrared to visible ratio of approximately 1.25, ethyl alcohol (EtOH) generates an infrared to visible ratio of approximately 1.5, and butanol (BuOH) generates an infrared to visible ratio of approximately 1.75. Accordingly, each of the foregoing solvents can be readily identified according to its relevant ratio, and therefore any imaging process can be enhanced as each solvent carries a substantially unique output signal ratio.

The present invention has been described with reference to its preferred embodiments so as to enable any person skilled in the art to make or use the present invention. However, various modifications to these embodiments will be readily apparent to those skilled in the art, and the generic principles defined herein may be applied to other embodiments without departing from the spirit or scope of the invention as set forth in the following claims.

What is claimed is:

1. A coherent imaging system comprising:
    a light source adapted to provide coherent light to illuminate a sample resulting in two or more optically mixed coherent signals;
    a detector adapted to receive the two or more optically mixed coherent signals corresponding to one or more frequencies of light in the optically mixed coherent signals;
    a processor connected to the detector and adapted to ratio two of the two or more optically mixed coherent signals in response to the output signal received by the detector and to generate an image in response to the ratioed optically mixed coherent signals; and
    a display connected to the processor and adapted to display the image generated by the processor.

2. The system of claim 1, wherein the light source comprises two or more lasers adapted to generate laser light of a predetermined frequency.

3. The system of claim 2, wherein the two or more lasers comprise a laser operating at approximately 790 nm and a laser operating at approximately 1037 nm.

4. The system of claim 1, further comprising an optical element disposed between the light source and the sample, the optical element adapted to focus the coherent light onto the sample.

5. The system of claim 1, wherein the processor is further adapted to ratio the two optically mixed coherent signals in response to variable frequency combinations of the coherent light.

6. The system of claim 1, wherein the detector comprises a photodetector.

7. A method of generating a coherent image comprising:
illuminating a sample with coherent light, thereby causing the sample to generate two or more optically mixed coherent signals;
receiving the two or more optically mixed coherent signals from the illuminated sample;
ratioing two of the two or more optically mixed coherent signals; and
generating an image in response to the ratioed optically mixed coherent signals.

8. The method of claim 7, wherein the step of illuminating a sample with coherent light comprises controlling at least two lasers at predetermined frequencies.

9. The method of claim 7, further comprising the step of focusing the coherent light onto the sample.

10. The method of claim 7, further comprising the step of varying a combination of the coherent light.

11. The method of claim 10, further comprising the step of ratioing the two optically mixed coherent signals in response to the varying combinations of the coherent light.

12. The method of claim 10, wherein the step of varying a combination of the coherent light comprises varying a pulse duration of at least two lasers operating at predetermined frequencies.

13. A coherent imaging system comprising:
a light source adapted to illuminate a sample with light resulting in two or more optically mixed coherent signals;
a detector adapted to receive the two or more optically mixed coherent signals;
a processor connected to the detector and adapted to ratio two of the two or more optically mixed coherent signals received by the detector and to generate an image in response to the ratioed optically mixed coherent signals; and
a display connected to the processor and adapted to display the image generated by the processor.

14. The system of claim 13, wherein the light source comprises a laser having a predetermined frequency.

15. The system of claim 13, wherein the detector comprises a photodetector.

16. The system of claim 13, wherein the processor is further adapted to ratio the two optically mixed coherent signals in response to successive illuminations of the sample.

17. The system of claim 13, further comprising an optical element disposed between the light source and the sample, the optical element adapted to focus the light from the light source onto the sample.

* * * * *